US00PP26976P2

(12) United States Plant Patent
Parks

(10) Patent No.: US PP26,976 P2
(45) Date of Patent: Jul. 26, 2016

(54) ***RHODODENDRON* PLANT NAMED 'LAVJ2011'**

(50) Latin Name: *Rhododendron hybrida*
Varietal Denomination: LavJ2011

(71) Applicant: Kathryn Forbes, Arlington, VA (US)

(72) Inventor: Joe B. Parks

(73) Assignee: University of Southern Maine, Portland, ME (US)

( * ) Notice: Subject to any disclaimer, the term of this patent is extended or adjusted under 35 U.S.C. 154(b) by 103 days.

(21) Appl. No.: 14/121,375

(22) Filed: Aug. 26, 2014

(51) Int. Cl.
*A01H 5/00* (2006.01)

(52) U.S. Cl.
USPC ..... Plt./238

(58) Field of Classification Search
USPC ..... Plt./238
See application file for complete search history.

*Primary Examiner* — Susan McCormick Ewoldt
(74) *Attorney, Agent, or Firm* — C. A. Whealy

(57) ABSTRACT

A new and distinct cultivar of *Rhododendron* plant named 'LavJ2011', characterized by its intermediate height; upright, outwardly spreading and mounding plant habit; freely branching habit; dense and bushy plant form; dark green-colored leaves; freely flowering habit; large bright purple-colored flowers; and good garden performance and winter hardiness.

2 Drawing Sheets

Botanical designation: *Rhododendron hybrida.*
Cultivar denomination: 'LavJ2011'.

BACKGROUND OF THE INVENTION

The present Invention relates to a new and distinct *Rhododendron* plant, botanically known as *Rhododendron hybrida*, an Elepidote-type *Rhododendron* and hereinafter referred to by the name 'LavJ2011'.

The new *Rhododendron* plant is a product of a planned breeding program conducted by the Inventor in Dover, N.H. The objective of the breeding program is to develop new freely-flowering *Rhododendron* plants with attractive leaves and flowers and low temperature tolerance.

The new *Rhododendron* plant originated from a cross-pollination made by the Inventor in 1990 of *Rhododendron hybrida* 'Dexter's Purple', not patented, as the female, or seed, parent with *Rhododendron hybrida* 'Florence Parks', not patented, as the male, or pollen, parent. The new *Rhododendron* plant was discovered and selected by the Inventor as a single flowering plant within the progeny of the stated cross-pollination in a controlled environment in Dover, N.H.

Asexual reproduction of the new *Rhododendron* plant by softwood cuttings taken in a controlled environment in Dover, N.H. since 1990 has shown that the unique features of this new *Rhododendron* plant are stable and reproduced true to type in successive generations.

SUMMARY OF THE INVENTION

Plants of the new *Rhododendron* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'LavJ2011'. These characteristics in combination distinguish 'LavJ2011' as a new and distinct *Rhododendron* plant:

1. Intermediate in height, upright, outwardly spreading and mounding plant habit.
2. Freely branching habit, dense and bushy plant form.
3. Dark green-colored leaves.
4. Freely flowering habit.
5. Large bright purple-colored flowers.
6. Good garden performance and winter hardiness.

Plants of the new *Rhododendron* differ primarily from plants of the female parent, 'Dexter's Purple', in the following characteristics:

1. Flowers of plants of the new *Rhododendron* are darker purple in color than flowers of plants of 'Dexter's Purple'.
2. Plants of the new *Rhododendron* are more winter-hardy than plants of 'Dexter's Purple'.

Plants of the new *Rhododendron* differ primarily from plants of the male parent, 'Florence Parks', in flower color as flowers of plants of 'Florence Parks' are darker purple in color than flowers of plants of the new *Rhododendron.*

Plants of the new *Rhododendron* can be compared to plants of 'Purple Passion', disclosed in U.S. Plant Pat. No. 9,981. Plants of the new *Rhododendron* differ primarily from plants of 'Purple Passion' in winter hardiness as plants of the new *Rhododendron* are more winter-hardy than plants of 'Purple Passion'. In addition, plants of the new *Rhododendron* and 'Purple Passion' differ slightly in flower color.

BRIEF DESCRIPTION OF THE PHOTOGRAPHS

The accompanying colored photographs illustrate the overall appearance of the new *Rhododendron* plant showing the colors as true as it is reasonably possible to obtain in colored reproductions of this type. Colors in the photographs may differ slightly from the color values cited in the detailed botanical description which accurately describe the colors of the new *Rhododendron* plant.

The photograph on the first sheet comprises a side perspective view of a typical flowering plant of 'LavJ2011' grown in a ground bed.

The photograph on the second sheet is a close-up view of a typical flowering plant of 'LavJ2011'.

DETAILED BOTANICAL DESCRIPTION

The aforementioned photographs and following observations and measurements describe plants grown in ground beds and two-gallon containers during the spring in a polyethylene-covered greenhouse in Grand Haven, Mich. and under cultural practices typical of commercial *Rhododendron* production. Plants were two years old when the photographs and description were taken. In the following description, color references are made to The Royal Horticultural Society Colour Chart, 1995 Edition, except where general terms of ordinary dictionary significance are used.

Botanical classification: *Rhododendron hybrida* 'LavJ2011'.

Parentage:

*Female, or seed, parent.*—*Rhododendron hybrida* 'Dexter's Purple', not patented.

*Male, or pollen, parent.*—*Rhododendron hybrida* 'Florence Parks', not patented.

Propagation:

*Type*.—By softwood cuttings.

*Time to initiate roots, summer*.—About 45 days at temperatures about 26° C.

*Root description*.—Fine, fibrous; typically white in color.

Plant description:

*Plant form and growth habit*.—Perennial and evergreen flowering shrub; intermediate in size, upright, outwardly spreading and mounding plant habit; freely branching habit; dense and bushy plant form; vigorous growth habit; freely flowering habit with numerous showy single type flowers.

*Branching habit*.—Freely branching habit with six primary lateral branches developing per plant; pinching (removal of terminal apex) enhances lateral branch development.

*Plant height*.—About 52 cm.

*Plant diameter, area of spread*.—About 45 cm.

*Lateral branch description*.—Length: About 30 cm. Diameter: About 5 mm. Internode length: About 6 cm. Strength: Strong. Aspect: About 20° from vertical. Texture, developing: Pubescent. Texture, mature: Pubescent, woody. Color, developing: Close to 144D. Color, developed: Close to 175A.

*Leaf description*.—Arrangement: Alternate; simple. Length: About 11.5 cm. Width: About 5.5 cm. Shape: Lanceolate to elliptic; cupped downward. Apex: Acute. Base: Cuneate. Margin: Entire. Venation pattern: Pinnate; reticulate. Texture, upper and lower surfaces: Smooth, glabrous. Luster: Glossy. Color: Developing leaves, upper surface: Close to 146B. Developing leaves, lower surface: Close to 145A. Fully expanded leaves, upper surface: Close to 139A; venation, close to 139A. Fully expanded leaves, lower surface: Close to 146C; venation, close to 145C. Petioles: Length: About 1.5 cm. Diameter: About 4 mm. Texture, upper and lower surfaces: Smooth, glabrous. Color, upper surface: Close to 183C. Color, lower surface: Close to 145A.

Flower description:

*Flower arrangement and appearance*.—Single type flowers arranged in terminal umbel-like racemes with usually about 22 per truss; inflorescences roughly hemispherical in shape; flowers face upward or outwardly; flowers campanulate with a single whorl of five to seven petals.

*Natural flowering season*.—Plants flower in May in Grand Haven, Mich.; flowers not persistent.

*Fragrance*.—Slightly sweet.

*Inflorescence height*.—About 10 cm.

*Inflorescence diameter*.—About 27 cm.

*Flower diameter*.—About 5.8 cm.

*Flower depth*.—About 2.5 cm.

*Flower buds*.—Length: About 2 cm. Diameter: About 1 cm. Shape: Lanceolate to elliptic. Color: Close to 146C.

*Petals*.—Arrangement: Single whorl of five to seven petals fused at the base forming a campanulate-shaped corolla. Length: About 3.9 cm. Width: About 2.7 cm. Lobe shape: Ovate to oblong. Apex: Obtuse to retuse. Margin: Entire; slightly undulate. Texture, upper and lower surfaces: Smooth, glabrous; silky. Color: When opening, upper surface: Close to 77B; towards the margins, close to 81B; throat, speckles, close to 144B and towards the edges of speckles, close to 146B. When opening, lower surface: Close to 74B; towards the margins, close to 81B. Fully opened, upper surface: Close to 77B; towards the margins, close to 81B; throat, speckles, close to 145A and towards the edges of speckles, close to 146B. Fully opened, lower surface: Close to 74B; towards the margins, close to 81B.

*Bud scales*.—Quantity: About 31. Length: About 4.7 cm. Width: About 2.5 cm. Shape: Deltoid. Apex: Obtuse. Base: Fused. Margin: Entire. Texture, upper and lower surfaces: Smooth, glabrous. Color: When opening:, upper and lower surfaces: Close to 146C. Fully opened, upper surface: Towards the base, close to 145D; towards the apex, close to 146C. Fully opened, lower surface: Towards the base, close to 145D; towards the apex, close to 146B.

*Peduncles*.—Length: About 5 cm. Diameter: About 8 mm. Angle: Mostly upright to outwardly. Strength: Strong. Texture: Smooth, glabrous. Color: Close to 145B; towards the apex, close to 145D.

*Pedicels*.—Length: About 1.7 cm. Diameter: About 2 mm. Angle: Mostly upright to outwardly. Strength: Strong. Texture: Smooth, glabrous. Color: Close to 145A.

*Reproductive organs*.—Androecium: Quantity of stamens per flower: About nine to eleven. Anther shape: Oblong. Anther length: About 1 mm to 2 mm. Anther color: Close to 74D. Pollen amount: Scarce. Pollen color: Close to 155A. Gynoecium: Pistil length: About 3.4 cm. Stigma shape: Oblong. Stigma color: Close to 59A. Style length: About 2.7 cm. Style color: Close to 58B to 58D. Ovary color: Close to 143A.

*Fruits and seeds*.—Fruit and seed development have not been observed on plants of the new *Rhododendron*.

Garden performance: Plants of the new *Rhododendron* have been observed to have good garden performance and to be tolerant to rain, wind and to be winter hardy to USDA Hardiness Zone 4.

Disease & pest resistance: Plants have not been observed to be resistant to pathogens and pests common to *Rhododendron* plants.

It is claimed:

1. A new and distinct cultivar of *Rhododendron* plant named 'LavJ2011' as illustrated and described.

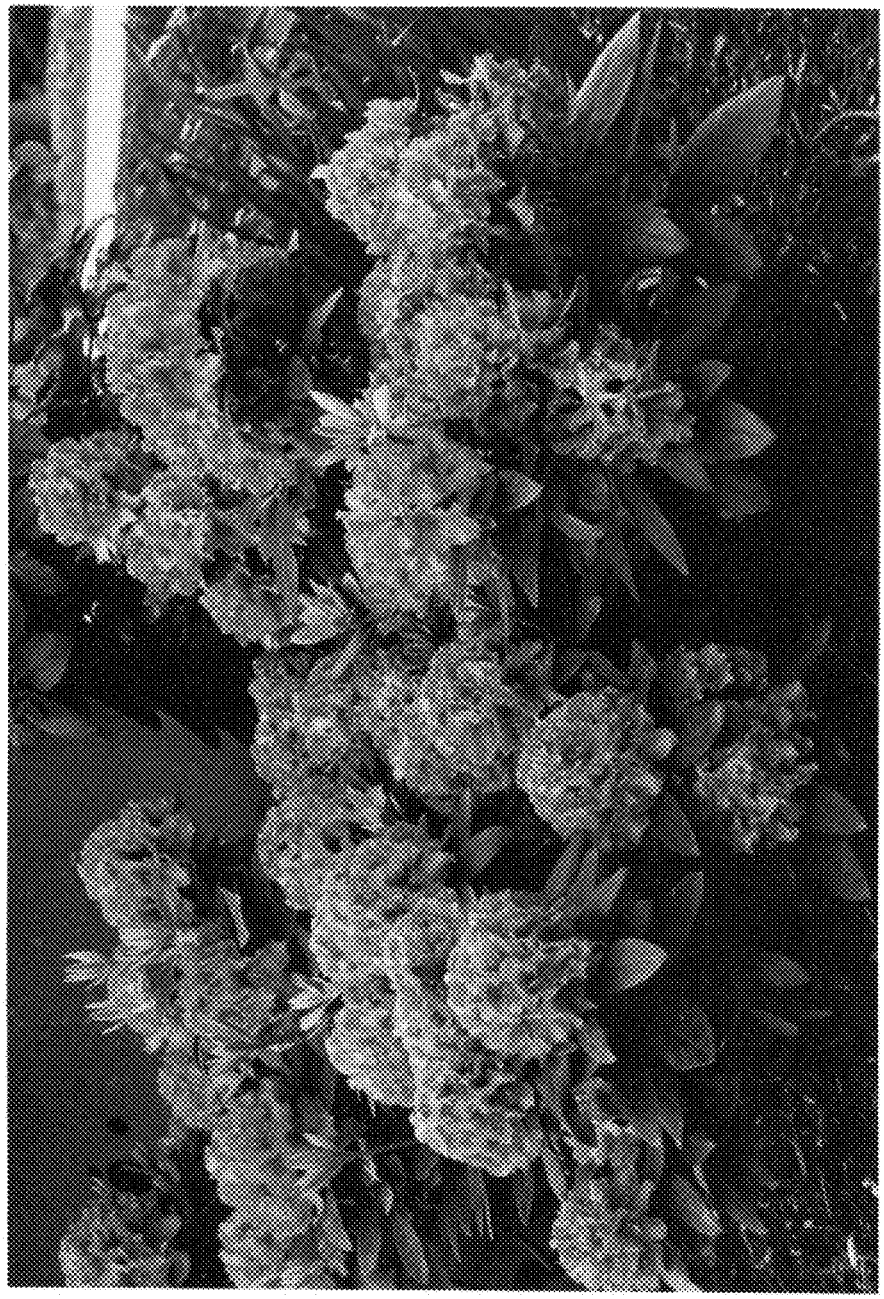

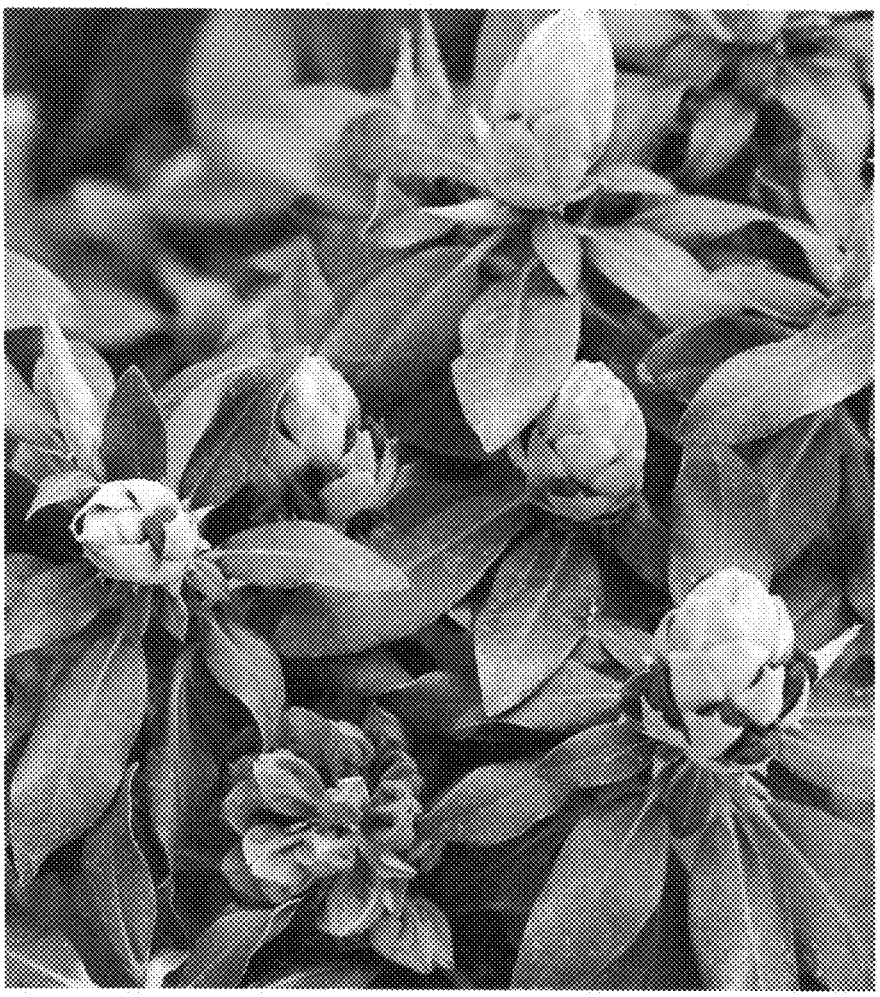

* * * * *